(12) United States Patent
Cohn et al.

(10) Patent No.: US 9,617,201 B2
(45) Date of Patent: Apr. 11, 2017

(54) FIXED BED PROCESS FOR CLAY CATALYZED ALKYLATION OF AROMATIC AMINES

(71) Applicant: CHEMTURA CORPORATION, Middlebury, CT (US)

(72) Inventors: Mitchel Cohn, West Haven, CT (US); Ronald Abbott, New Hartford, CT (US); Alan B. True, New Haven, CT (US); Huiyuan Chen, Cheshire, CT (US)

(73) Assignee: CHEMTURA CORPORATION, Middlebury, CT (US)

( * ) Notice: Subject to any disclaimer, the term of this patent is extended or adjusted under 35 U.S.C. 154(b) by 14 days.

(21) Appl. No.: 14/509,123

(22) Filed: Oct. 8, 2014

(65) Prior Publication Data

US 2015/0105588 A1    Apr. 16, 2015

Related U.S. Application Data

(60) Provisional application No. 61/890,392, filed on Oct. 14, 2013.

(51) Int. Cl.
*C07C 209/68* (2006.01)
*C07C 211/55* (2006.01)
*C07C 211/58* (2006.01)

(52) U.S. Cl.
CPC .......... *C07C 209/68* (2013.01); *C07C 211/55* (2013.01); *C07C 211/58* (2013.01); *Y02P 20/582* (2015.11)

(58) Field of Classification Search
None
See application file for complete search history.

(56) References Cited

U.S. PATENT DOCUMENTS

| 2,943,112 | A | | 6/1960 | Popoff et al. |
| 3,496,230 | A | | 2/1970 | Kaplan et al. |
| 4,740,620 | A | * | 4/1988 | Dixon ................ C07C 209/68 502/73 |
| 4,824,601 | A | | 4/1989 | Franklin |
| 5,214,211 | A | | 5/1993 | Kurek et al. |
| 5,672,752 | A | | 9/1997 | Lai et al. |
| 5,750,787 | A | | 5/1998 | Lai et al. |

(Continued)

FOREIGN PATENT DOCUMENTS

| EP | 0 387 979 A1 | 9/1990 |
| EP | 1939169 A2 | 7/2008 |
| WO | 2010/017030 A1 | 2/2010 |

OTHER PUBLICATIONS

Chitnis et al. Journal of Catalysis 1996, 84-94.*
Written Opinion dated Nov. 30, 2016 issued by IPOS in corresponding SG Application No. 11201601762R, 5 pages.

*Primary Examiner* — Clinton Brooks
(74) *Attorney, Agent, or Firm* — Dilworth IP LLC

(57) ABSTRACT

Aromatic amines, for example, diarylamines such as diphenylamine, dinaphthylamine, N-phenyl-N-naphthyl amine etc., are alkylated by passing a mixture of the amine and an olefin, though a clay catalyst in a fixed bed reactor system. The process is conveniently run as a continued process, produces an alkylated aromatic amine in excellent purity and provides efficiencies in material and energy use.

10 Claims, 2 Drawing Sheets

(56) References Cited

U.S. PATENT DOCUMENTS

| | | | |
|---|---|---|---|
| 5,817,831 A * | 10/1998 | Rhubright | C07D 209/86 502/117 |
| 6,204,412 B1 | 3/2001 | Lai | |
| 6,315,925 B1 | 11/2001 | Aebli et al. | |
| 6,355,839 B1 | 3/2002 | Onopchenko | |
| 8,828,916 B2 | 9/2014 | Simard | |

* cited by examiner

FIXED BED PROCESS FOR CLAY CATALYZED ALKYLATION OF AROMATIC AMINES

This application claims benefit under 35 USC 119(e) of U.S. Provisional Application No. 61/890,392 filed Oct. 14, 2013, the disclosure of which is incorporated herein by reference.

Provided is an improved process, readily run as a continuous process, for alkylating aromatic amines, for example, diarylamines such as diphenylamine, dinaphthylamine, N-phenyl-N-naphthyl amine etc., with an olefin, whereby a mixture of the aromatic amine and the olefin are passed through a clay catalyst in a fixed bed reactor system.

BACKGROUND OF THE INVENTION

Alkylated aromatic amines, e.g., diarylamines, such as alkylated diphenylamine, are well known in the art to be effective stabilizers/antioxidants in a wide variety of organic materials, for example, polymeric substances such as natural or synthetic rubber, other elastomers and plastics, lubricating oils including e.g., mineral oil derived lubricants and synthetic lubricants, etc. In many these applications, light colored products which are liquid at room temperature are desirable for a number of practical reasons.

Alkylation of diarylamines, such as diphenylamine, with olefins in the presence of suitable alkylation catalysts is well known in the art. For example, U.S. Pat. No. 2,943,112 discloses a two-step process whereby alkylation of diphenylamine, in the presence of acid catalysts or clay catalysts, with relatively unreactive olefins, such as secondary alkenes, is followed by an alkylation reaction with more reactive olefins to scavenge the unreacted diphenylamine, with clay catalysts providing the desired light color. The reaction can be run in a closed reactor at elevated pressure.

U.S. Pat. No. 3,496,230 discloses the preparation of a mixture of 80% dinonydiphenylamine and 15% nonyldiphenylamine in the presence of Friedel-Crafts catalysts such as $AlCl_3$ and $ZnCl_2$, but mixtures contaminated by traces of chlorine, metal compounds and undesirable by-products, e.g. N-alkylated diphenylamines and diphenylamines alkylated in the 2- and 2'-positions, are obtained which are black in color and very viscous.

European Patent Application No. 387 979 discloses the reaction of diphenylamine with an eight-fold excess of tripropylene carried out in the presence of large quantities of acid-activated clays and under reflux conditions.

U.S. Pat. No. 4,824,601 discloses the use of acidic clay catalysts for the alkylation of diphenylamine to produce a light colored, liquid product by reacting certain molar ratios of reactants within specific temperature ranges for a time sufficient to ensure the alkylated product contains less than 25% dialkylated diphenylamine. The limit on the amount of dialkylated diphenylamine is disclosed as necessary to avoid the formation of crystallized, solid products.

U.S. Pat. Nos. 5,672,752 and 5,750,787 disclose processes for alkylating diphenylamine with linear alpha olefins and diisobutylene in the presence of a clay catalyst, which selectively result in a higher proportion of monoalkylated diphenylamine and a lower proportion of unsubstituted diphenylamine and/or disubstituted or polysubstituted diphenylamines. Conditions favoring mono-alkylation are disclosed. U.S. Pat. No. 6,204,412 discloses a method of alkylating diphenylamine to obtain a light colored, liquid product, which comprises a two-step method wherein, in the second step, a second olefin is added to the reaction mixture containing diphenylamine and diisobutylene (and/or an alpha-olefin of the disclosed formula) to scavenge or reduce the amount of unreacted diphenylamine in the product U.S. Pat. No. 6,315,925 discloses a process comprising alkylating diphenylamine with an excess of nonene or a mixture of isomeric nonenes in the presence of from 2.0 to 25.0% by weight, based on diphenylamine, of an acidic clay in the absence of a free protonic acid, resulting in a mixture containing at least 68.0% dinonyldiphenylamine, from 20.0 to 30.0% nonyldiphenylamine, not more than 3.5% trinonyldiphenylamine; and not more than 1.0% diphenylamine.

U.S. Pat. No. 6,355,839 discloses a process for preparation of alkylated diphenylamine antioxidant which comprises alkylating diphenylamine with a polyisobutylene in the presence of a clay catalyst, wherein the polyisobutylene has an average molecular weight in the range of 120 to 600 and wherein the polyisobutylene contains at least 25% methylvinylidene isomer.

U.S. Pat. No. 8,828,916 discloses a process for preparing nonylated diphenylamines which improves nonenes usage by recycling and reusing stripped unreacted nonenes from an earlier process. The process comprises consecutive recycle of recovered nonenes is conducted at a sequential two step temperature reaction. The nonene alkylated diphenylamine product mixture is a useful antioxidant when added to a lubricating composition.

There is still a need however for a more efficient and less expensive process for alkylating aromatic amines that will provide a high quality product with low color in a controllable manner.

Fixed bed reactors for catalytic reactions are known. One advantage of fixed bed reactors over, e.g., standard reaction kettles, is that they are readily adapted to continuous processes which can be used to control contact times with the catalyst by varying feed rates. Another advantage is the excellent heat transfer and control capability. Conceptually simple, one rudimentary fixed bed reactor useful for the present catalytic alkylation is a tube or column with a porous support at one end for preventing flow through of catalyst. The catalyst is loaded into the tube or column and reactants are passed through. The rate at which the reactants progress through the catalyst determines the residence time.

Of course, the shape of the fixed bed reactor is not limited to the rudimentary device above and a variety of geometries and sizes are known. Multibed reactors comprising several fixed bed reactors, typically in parallel, are common. Multiple passes can be used in a process if desired and it is possible to arrange two or more reactors in series. When using more than one single tube or multibed reactor, each reactor can contain the same or different catalyst, be of equal or different volume, heated or cooled at the same or different temperatures. It is also possible for the reactant composition to be the same or different in different reactors, for example, additional amounts of an alkylating agent, or in some embodiments a different reactive species, may be fed into a downstream reactor along with the reaction mixture produced in a previous reactor,

SUMMARY OF THE INVENTION

The present invention provides an improved process for alkylating aromatic amines, for example, diarylamines such as diphenylamine, dinaphthylamine, N-phenyl-N-naphthyl amine etc., with olefins, e.g., nonenes, isobutylene, oligomers of isobutylene, oligomers of propylene, styrenes etc., using a clay catalyst in a fixed bed reactor system, e.g., plug flow, fixed bed reactor system. The process of the invention eliminates the need for various processing steps, e.g., there is no need for a separate step to isolate the catalyst from the product mixture etc., and is conveniently run as a continuous process. In many embodiments the reaction is run at temperatures above the boiling point of one or more is the reactants and can be run under pressure.

The products obtained are low in color and can comprise predominately a single compound, but liquid products comprising mixtures of alkylated aromatic amines can also be prepared. For example, in the alkylation of diphenylamine with nonenes, a mixture of mono-alkyl and di-alkyl diphenyl amine, plus a minor or negligible amount of trialkyl diphenyl amine, is often obtained, which mixture is liquid at room temperature. Proper selection of catalyst, catalyst amount and catalyst preparation, e.g., catalyst conditioning, reaction temperature, mole ratios of alkylating olefin to aromatic amine, flow rates etc., can be varied to optimize product distribution.

The process of the invention is also flexible in that a number of reactor systems can be employed, e.g., the reactor system can employ a single reactor including a multibed reactor, or a series of reactors, the reactor can be closed or vented, multiple temperature zones may be employed, multiple reactant feeds can be introduced e.g., to allow for further introduction of reactants, internal recycling of recovered reactants, or to alter the composition of the reaction mixture, etc. It is also possible for the process to include using multiple alkylation steps for greater control of temperature, reaction rates, product distribution etc.

DESCRIPTION OF THE INVENTION

Figure 1:
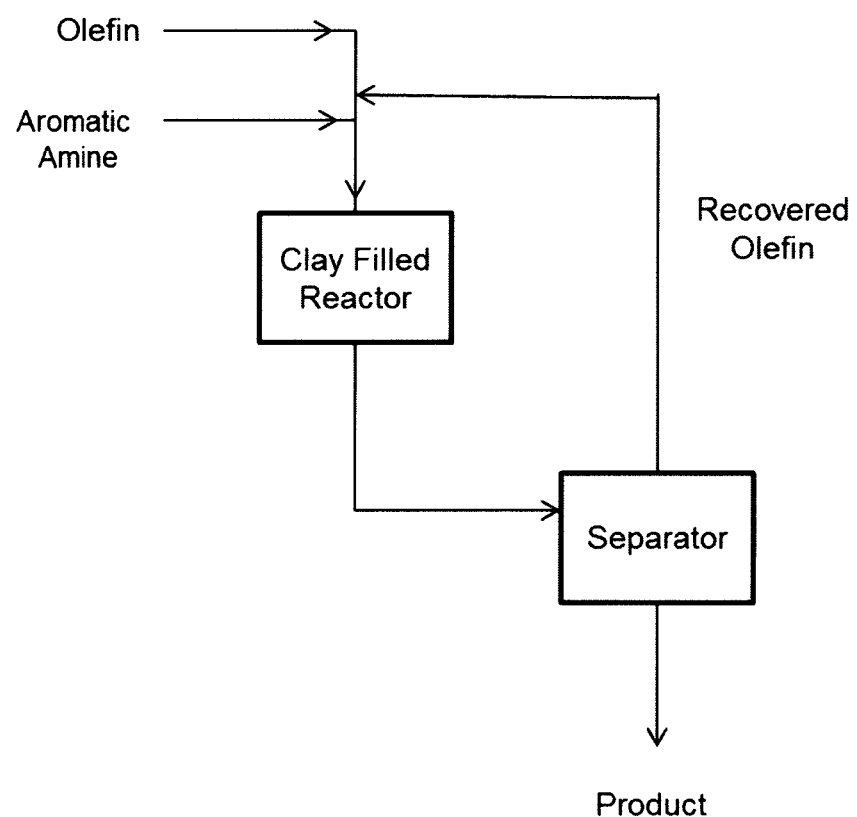
FIG. 1 is a block diagram of one embodiment of the invention showing the progress of the reaction and recovery of excess olefin in a simplified reaction setup

One broad embodiment of the invention provides a process for alkylating an aromatic amine comprising:

a) loading a fixed bed reactor with an acidic clay, b) heating or cooling the reactor to within a selected temperature range, e.g., from about 50° C. to about 250° C., c) passing through the acidic clay in the fixed bed reactor a mixture comprising one or more olefins selected from the group of $C_{3-20}$ olefins, and an aromatic amine of formula:

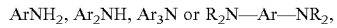

wherein each Ar of the aromatic amine starting material is independently selected from the group consisting of phenyl, phenyl substituted by $C_{1-18}$ alkyl, naphthyl, and naphthyl substituted by $C_{1-18}$ alkyl;

and each R is independently selected from the group consisting of H, $C_{1-18}$ alkyl, phenyl, phenyl substituted by $C_{1-18}$ alkyl, naphthyl, and naphthyl substituted by $C_{1-18}$ alkyl;

to yield a product wherein one or more of the groups Ar are alkylated by one or more alkyl groups derived from the $C_{3-20}$ olefin.

The process of the invention is most efficiently run as a continuous process.

The present process may be used in the alkylation of a variety of aromatic amines, i.e., mono-di-, and tri-aromatic amines and diamino aromatics, for example diphenylamine, dinaphthylamine, N-phenyl-1-naphthylamine, N-phenyl-2-naphthylamine, p,p'-phenylenediamine, p-amino-diphenylamine, p-methylamino-diphenylamine and p-isopropylamino-diphenylamine.

In many embodiments the aromatic amine being alkylated is of formula:

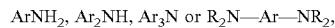

wherein each Ar is independently selected from the group consisting of phenyl, phenyl substituted by $C_{1-12}$ alkyl, naphthyl, and naphthyl substituted by $C_{1-12}$ alkyl; for example phenyl, phenyl substituted by $C_{1-12}$ alkyl or naphthyl; for example, phenyl, phenyl substituted by $C_{1-9}$ alkyl or naphthyl;

and each R is independently selected from the group consisting of H, $C_{1-18}$ alkyl, phenyl, phenyl substituted by $C_{1-18}$ alkyl, and naphthyl, e.g., H, $C_{1-12}$ alkyl, phenyl or phenyl substituted by $C_{1-12}$ alkyl; e.g., H, $C_{1-12}$ alkyl, phenyl.

Certain embodiments relate to the alkylation of an aromatic amine of formula $Ar_2NH$ or $R_2N-Ar-NR_2$, for example, $Ar_2NH$.

The $C_{3-20}$ olefins used in the present method are well known and include propene, butene, pentene, hexene, octene, nonene, mixtures of nonenes, decene, undecene, dodecene, tetradecene, hexadecene octadecene and the like, including straight chain or branched isomers and isomers differing by the placement of the double bond, for example, 1-nonene, 2-nonene etc., and n-butene, iso-butene, isooctene, 2-ethylhexene and the like. Mixtures of olefins are often employed. In some select embodiments the olefins are derived from propene or isobutylene, e.g., certain embodiments the one or more olefins comprise one or more of isobutylene, di-isobutylene, tri-isobutylene, di-propylene, tri-propylene and the like. Often, the olefin will comprise mixtures of propylene and butylene oligomers, e.g., oligomer mixtures comprising propylene or butylene dimers, trimers and/or tetramers etc., which mixtures often include the monomeric species. In certain embodiments the one or more olefins comprise isobutylene, di-isobutylene, tri-isobutylene, di-propylene, tri-propylene or tetrapropylene.

The reactions are often run under pressures greater than atmospheric. In some cases this is due the pressure created by forcing the reactants through the catalyst and a specified flow rate. In the case of very volatile olefins, e.g., propene, butene and iso-butene, and when the selected olefin has a boiling point below the reaction temperature, higher pressure is highly desired.

In many embodiments the one or more olefins is selected from the group of $C_{6-18}$ olefins, for example, $C_{8-18}$ olefins or $C_{8-12}$ olefins, such as diisobutylene and nonenes. In many cases, such as when nonene is obtained by trimerization of propylene, a mixture of nonenes will be present.

The mole ratio of the one or more olefins to the aromatic amine is generally from about 0.8 or about 1:1 to about 5:1, e.g., from about 1:1 to about 4:1 or from about 1:1 to about 3:1. While the process can be run using equimolar amounts of olefin and amine, it is generally run using a higher amount of olefin, for example, the mole ratio of the one or more olefins to the aromatic amine is often from about 1.1:1, 1.2 or 1.3 to about 5:1 or 4:1, e.g., from about 1.3:1 to about 4:1, from about 1:5 to about 4:1, or from about 2:1 to about 4:1. Unreacted amine, olefin or olefin byproducts, e.g., olefin oligomers or cracking products, can be removed from the product mixture using standard techniques, such as distillation.

In general, yields of alkylated amines are high based on starting amine, e.g., 75% to 100%, typically higher than 80 or 85%, and in many embodiments the yield of alkylated amines based on starting amine is 90%, 95% or greater. In the event that too large a quantity of unreacted amine remains, a number of known methods to reduce the amount of unreacted amines, such as reaction with highly reactive olefins, e.g., styrene, may be employed, however, this is not a regular occurrence.

The clays of the invention are aluminosilicates and may be naturally occurring, such as bauxite or mordenite clay, or a synthetic material and may comprise alumina, silica, magnesia, zirconia or other compound exhibiting similar properties. Clays have long been used in alkylation of aromatic amines and typically provide low color products as opposed to, e.g., metal halide catalysts such as aluminum trichloride. Many clays effective in the present process are commercially available and are described or referenced in the above cited art.

Clays useful as catalysts in the present invention are typically "acid treated clays", "acid activated clays" or "acidic clays", the terms used interchangeably herein, and include those used for bleaching oils and waxes. For example, useful clays include sub-bentonite or bentonite clays, consisting predominantly of the clay mineral montmorillonite, which are characterized by rapid slaking when it is in the air dried state and only a slight swelling when placed in water. Acid active bentonite clays useful as catalysts include F24X, F-24, F20X, F22B presently sold by BASF, formerly from ENGELHARD. Other commercially available clays are suitable for use in the present invention, including those sold as FILTROL 24, FILTROL 25 and FILTROL 62, FULCAT 14, FULCAT 22B, FULMONT 700C, FULMONT 237, KATALYSATOR, Attapulgus clay and Tonsil clay.

The clay catalysts may contain some water as received. Removal of the water prior to use is reported to result in a lighter colored product in similar reactions, e.g., U.S. Pat. No. 5,672,752. It has been found that removal of water can improve reaction kinetics of the inventive process and reduces dimerization of the olefin. Therefore it is desirable to use a low water content clay or to remove the water, for example, by vacuum stripping, heating the clay with a nitrogen sweep, azeotroping with organic liquids including olefins, or any other method known in the art.

In particular embodiments, the clay is F-24X, F-24 or F-22B which is pretreated to remove water, and in many of these embodiments the pretreatment also removes dust. For example, the catalyst is packed in a column and rinsed with twice its weight in methanol to remove dust and draw moisture out. The catalyst is then dried in an 80° C. oven overnight to evaporate methanol. If necessary, the catalyst can be further rinsed with a less polar and chemically inert solvent, such as heptane, for methanol removal before the drying step. In some embodiments of the invention, the water is removed by passing crude, unstripped reaction product or nonenes through the columns. Often, the bottom of the reactor tube may be packed with fine material (glass wool, sand, fine alumina or F-20X clay) to prevent the passage of catalyst dust.

Some clays used to alkylate aromatic amines in standard batch reactions run in kettles may not be optimum for use in the present invention under certain conditions for a variety of reasons. This is often due to physical properties of the clay, for example, the fine particle size of F-20X may lead to extra back-pressure as the reactants are passed through a column packed with this clay. Therefore, when using, e.g., F-20X clay, higher internal pressure may be required to move the reactants through the clay at the desired flow rate.

The reaction is typically run in a reactor heated at a temperature of from about 50° C. to about 250° C., for example from about 100° C. to about 200° C. and in some embodiments from about 140° C. to about 180° C. The reaction can be carried out at a single temperature or, sequentially, at different temperatures. In some cases, the reaction may cause enough of an exotherm which will require a means for dissipating excess heat. Adjusting the rate at which individual reactants are added may also impact the reaction temperature.

The starting materials may be preheated prior to introduction to the reactor. In some embodiments one or more of the reactants are solid at room temperature and the solid component or a mixture comprising the solid component is heated to a temperature to keep the component or the mixture liquid.

When alkylating aromatic amines, such as di-aryl amines, with an olefin using a standard batch process, the reaction is typically run at the temperatures above, the product mixture cooled and then filtered, transferred to a vessel where excess olefin is removed by distillation or stripping, and other steps to finish the product may occur. During this batch process there are several steps which require that the reaction/product mixture be heated and cooled. For example, the reactants are often heated for better handling before addition to the reactor, the reactor is heated, the product after reaction is cooled before final filtration, the product mixture is then reheated to strip off the excess olefin after which the product is allowed to cool.

By using the fixed bed reactor the present process eliminates the need for filtering the product, and dispenses with the need to provide agitation to the reaction. Other process efficiencies are also readily realized. For example, the reactants are typically passed through the clay filled reactor bed or beds at the reaction temperature, the product mixture is collected at elevated temperature while excess olefin is continuously stripped out and fed back into the reactor. The need to cool, filter and reheat the product mixture for stripping the excess olefin is eliminated. A simplified reactor scheme is shown in FIG. 1. The practitioner can immediately envision from the scheme that additional reactors and feed lines can be added, tanks for mixing reactants prior to introduction to the catalysts can be inserted as well as valves and other controls, etc. In FIG. 1, heating can be carried out anywhere along the reaction train, for example, reactant holding tanks, mixing tanks, feed lines, reactors, etc.

In one embodiment, the reactors are the tubes of shell and tube heat exchangers filled with the catalyst where the shell is used to maintain temperature control of the reaction mixture.

Figure 2:
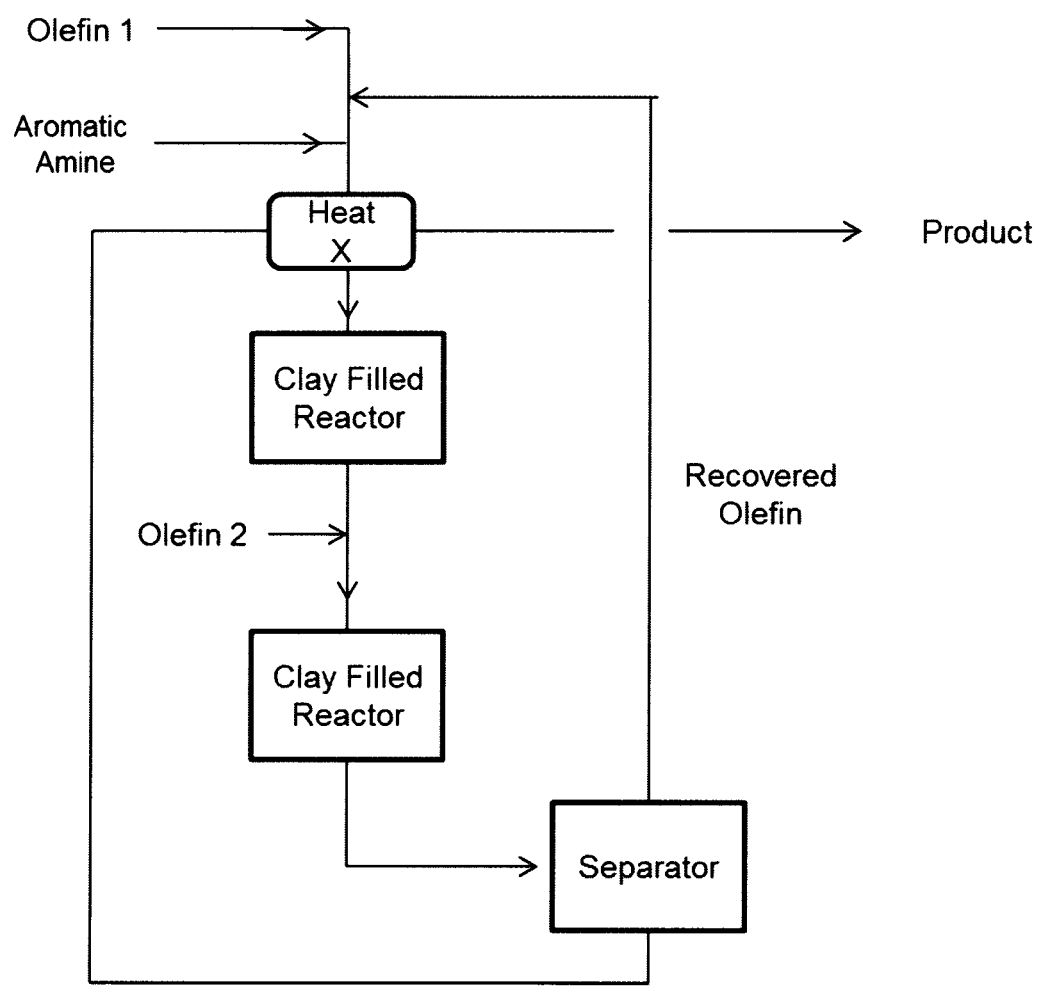
FIG. 2 is a block diagram of a further embodiment of the invention showing the use of the reaction product as heat exchanger fluid

A sampling of additional design elements are illustrated by the simplified scheme shown in FIG. 2, including an additional reactor and additional olefin feed line. Variations on the design of FIG. 2 could include elimination of olefin feed 1 or olefin feed 2, inclusion of additional feeds and/or reactors, etc. FIG. 2 also references the use of heat exchangers in the reaction apparatus design which can be used as economizers. The economizers allow one to transfer the heat from one stream of the system to cool another, saving both heating and cooling costs. For example, FIG. 2 illustrates passing the still hot product mixture through one or more heat exchanges positioned elsewhere in the reactor apparatus, which makes use of the heat given off during cooling of the product to preheat the reactor feed or feeds.

For example, the process of the invention is conveniently carried out in an apparatus comprising a shell and tube heat exchanger setup of parallel clay filled tubes to be used as fixed beds. Unreacted alkenes are typically fed in excess and continuously stripped off the crude product mixture directly after reaction. In particular embodiments, the reaction product is itself used as the heat exchanger fluid, typically without external cooling, often at or near the temperature at which it was collected. Removal of unreacted alkenes can be carried out under reduced pressure if desired.

If desired, the reaction can be carried out in a neutral solvent such as mineral oil or an inert hydrocarbon solvent, but generally no solvent is necessary. In some embodiments, the use of an excess of olefin can act as a solvent. Inert gas, such as nitrogen, can be used to minimize oxidation of products during reaction, but mostly to allow operation at higher temperatures with the lower boiling oligomers.

The olefin and aromatic amine reactants can be introduced into the reactor separately through different individual feeds, separately but through the same line, or they may be mixed together before being introduced to the fixed bed reactor through the same feed. For example, the reactants may be mixed together in a vessel and the resulting mixture may be introduced to the reactor through a single feed. It is also possible to introduce a reaction mixture into the reactor and then introduce additional doses of one or more reactants at a later point, often using additional feeds.

Typically, the reactants are pumped into and through the reactor. The rate of flow through the catalyst can thus be controlled by adjusting the pump. A certain amount of increased pressure within the reactor will generally exist due to the back pressure created by the flow of reactants though the catalyst bed or other points in the reactor system, faster feed rates generating higher pressure. It is also possible to draw the reactants through the reactor by pumping the reaction mixture out after passage through the reactor and control the flow rate by adjusting the post reactor pump.

Typically the pressure under which the reaction occurs is, at least partially, a function of the olefin used, the reaction temperature, the flow rate, and/or the clay catalyst selected. The reaction pressure can range up to about 250 psi or higher, but is often below about 250 psi, and frequently 100 psi or less and in some embodiments the reaction can be run at roughly atmospheric pressure.

One particular embodiment relates to the alkylation of diphenylamine providing alkylated diphenylamines, which are known as effective antioxidants, for example, reaction of diphenyl amine with nonenes, 2,4,4-trimethylpentene and the like produce commercially valuable alkylated diphenylamines, often as a mixture of mono- and di-alkylated compounds, many of which are liquids.

For example, the process can be employed to alkylate a diaryl amine to produce a product mixture which comprises:
less than 1% by weight of starting aromatic amine, based on all aromatic amines present,
about 15% to about 35% of mono-alkylated aromatic amine;
about 55% to about 80% di-alkylated aromatic amine; and
about 0.5 to about 15% of tri-alkylated aromatic amine.
For example:
less than 1% by weight of starting aromatic amine, based on all aromatic amines present,
about 15% to about 30% of mono-alkylated aromatic amine;
about 60% to about 80% di-alkylated aromatic amine; and
about 0.5 to about 10% of tri-alkylated aromatic amine.

In a select embodiment, the process is used to prepare a liquid mixture of nonylated diphenylamines comprising
less than 1% by weight of starting diphenylamine,
about 15% to about 35%, e.g., about 15% to about 30%, of mono-nonyldiphenyl amine;
about 55% to about 80%,e.g., 60% to about 80%, di-nonyldiphenyl amine; and
about 0.5 to about 15%, e.g., 0.5 to about 10% of tri-nonyldiphenyl amine, based on all aromatic amines present.

Other product ratios can be produced by varying the catalyst, flow rate etc., of the process.

EXAMPLES

Examples 1-7

Diphenylamine Substituted by Nonenes

Example 1

A stainless-steel tube (1 inch diameter, 13 inches in length) was charged with 92.0 grams of F-24 bentonite catalyst (20-60 mesh), which catalyst was pretreated to remove water. The reaction tube was placed vertically inside a tube furnace. The reaction temperature was set at 180° C. A six point thermocouple recorded the internal temperature of the reaction tube along its length. The set-temperature of the reaction was maintained on only the upper half of the tube and the bottom end maintained temperatures between 60-90° C. The nominal volume of the reactor was therefore estimated as the upper half, where set-temperatures were maintained. Nonenes and diphenylamine were mixed in a 2.9:1 mass ratio, i.e., 3.9:1 mole ratio (nonenes:DPA) and heated, from about 60° C. to about 130° C. to avoid precipitation of diphenylamine (mp 50-52° C.). The feed line connecting the reaction mixture to the reactor was also heated at from about 60° C. to about 130° C. The heated reactant mixture was pumped into the reactor at a mass flow rate between 12 and 13 grams per hour. Sample product fractions were collected in a round-bottom flask. Final filtration of the product was unnecessary as the catalyst was stationary during the process. The reactants were pumped through the reactor for a total of 340 hours. Samples were taken at intervals a-d, reaction time recorded as Catalyst Age, and analyzed by gas chromatography to determine the product ratio.

Examples 2 and 3 followed the procedure of Example 1 except that the flow rate was set at 8.4 grams per hour for Example 2 and 5.7 grams per hour for Example 3.

DPA conversion in each example was 99-100% and the product had a light color. Analysis of the product ratios are shown in Table 1.

TABLE 1

Results for Nonylation of Diphenylamine

| Ex/Interval | Flow Rate (g/h) | Catalyst Age (h) | % DPA | % Mono-alkylated | % Di-Alkylated | % Tri-Alkylated |
|---|---|---|---|---|---|---|
| 1/a | 12.9 | 58 | 0 | 18.6 | 73.0 | 6.5 |
| 1/b | 12.9 | 107 | 0 | 21.9 | 72.6 | 5.3 |
| 1/c | 12.9 | 207 | 0 | 27.3 | 69.3 | 3.6 |
| 1/d | 12.9 | 338 | 0.4 | 36.5 | 61.2 | 2.1 |
| 2 | 8.4 | 310 | 0 | 23.8 | 71.5 | 4.7 |
| 3 | 5.7 | 332 | 0 | 17.5 | 75.0 | 7.4 |

The reactions of Examples 4-7 were run similarly to that of Example 1; Examples 4-6 were run for over 1,000 hours while adjusting the flow rate and temperature to maintain the excellent conversion and product ratio obtained during the initial portion of the reaction, Example 7 was run for 300 hours. Data taken at early intervals and information on raw material feed, reaction conditions etc., are shown in Table 2 along with the data from Example 1, interval c.

Example 4

Following a procedure similar to that of Example 1, a stainless-steel tube (1 inch diameter, 13 inches in length) was charged with 104 grams of F-24X BASF catalyst (20-60 mesh), which catalyst was pretreated to remove water. The reaction tube was placed vertically inside a tube furnace. The reaction temperature was set at 155° C. A six point thermocouple recorded the internal temperature of the reaction tube along its length. Nonenes and diphenylamine were mixed in a 2.4:1 mass ratio, i.e., 3.2:1 mole ratio (nonenes: DPA) and heated, e.g., from about 60° C. to about 130° C. to avoid the precipitation of diphenylamine (mp=52° C.). The feed line connecting the reaction mixture to the reactor was also heated to pre-heat the reactants to about 130° C. The heated reactant mixture pumped into the reactor at a mass flow rate between 13 and 14 grams per hour. Sample product fractions were collected in reagent bottles at ambient temperature at various time intervals and analyzed by Gas Chromatography to determine the product and raw material ratio. Data recorded at 209 hours is shown in Table 2.

Example 5

The reaction was performed according to the procedure of Example 4 except that a 25 psig check valve was attached to the outlet of the tubular reactor, and the weight ratio of nonenes to DPA is reduced from 2.4 to 2.24, which reduces the mole ratio of nonenes to DPA from 3.2 to 3.0. The reaction is run under a pressure of 25 psig preventing evaporation of nonenes from the reaction mixture. Although less nonenes is used, the reaction rate improves by about 10%. Data recorded at 198 hours is shown in Table 2.

Examples 6

The reaction was performed according to the procedure of Example 5 except that the reaction temperature was set at 145° C. DPA conversion was 99-100% and the product in liquid form had a light color. Data recorded at 206 hours is shown in Table 2.

Examples 7

The reaction was performed according to the procedure of Example 5 except that the catalyst is FULCAT 22B granule of the same volume, which catalyst was pretreated to remove water. Data recorded at 215 hours is shown in Table 2.

DPA conversion in each of Examples 4-7 was 99-100% and the product had a light color. Analysis of the product ratios and information on raw material feed, reaction conditions, mass of effluent products and catalyst run time are shown in Table 2. Nonylated DPA amount and unreacted nonenes were estimated based on crude products' GC data. The temperature record point 6 is at the position of about 1 inch from the top of the tube, the temperature record point 1 is at the position of about 1 inch from the bottom of the tube, the temperature record point 4 is at the position of midpoint of tube and used as set point of temperature.

TABLE 2

Conditions and Results for Nonylation of Diphenylamine

| | Ex 4 | Ex 5 | Ex 6 | Ex 7 | Ex 1/c |
|---|---|---|---|---|---|
| Raw Materials and Catalyst | | | | | |
| Diphenylamine | 875 | 1017 | 856 | 889 | 690 |
| Nonenes | 2100 | 2278 | 1491 | 1990 | 2001 |
| Weight Ratio | 2.4:1 | 2.24:1 | 2:24:1 | 2.24:1 | 2.90:1 |
| Catalyst | F-24X | F-24X | F-24X | FULCAT 22B granule | F-24 |
| Catalyst particle size | 20-60 | 20-60 | 20-60 | 20-60 | 20-60 |
| Catalyst Amount (gram) | 104 | 106 | 104 | 86 | 92 |
| Reaction Conditions | | | | | |
| Temperature Set point (° C.) | 155 | 155 | 145 | 155 | 180 |
| Temp Record point-6 (° C.) | 148 | 160 | 137 | 159 | 145 |
| Temp Record point-4 (° C.) | 155 | 154 | 145 | 153 | 180 |
| Temp Record point-1 (° C.) | 94 | 150 | 113 | 138 | 95 |
| Pressure (psig) | — | 25 | 25 | 25 | — |
| Average Flow Rate (g/hour) | 14 | 16 | 10 | 13 | 13 |
| Run time (hours) | 209 | 198 | 206 | 215 | 207 |
| Results and Amounts of Crude and Finished Product | | | | | |
| Crude Product Amount (g) | 2944 | 3115 | 2056 | 2879 | 2690 |
| Unreacted Nonenes Amount (g) | 877 | 857 | 617 | 892 | 1447 |
| Product Amount (g) | 2066 | 2258 | 1439 | 1987 | 1243 |
| Product Compositions Calculated By GC Data | | | | | |
| Diphenylamine (DPA) | 0.10 | 0.20 | 0.07 | 0.14 | 0 |
| Mono-nonylated DPAs | 17.3 | 15.7 | 18.5 | 19.5 | 21.9 |
| Di-nonylated DPAs | 75.8 | 78.0 | 76.2 | 76.3 | 72.6 |
| Tri-nonylated DPAs | 6.8 | 6.1 | 4.8 | 3.8 | 5.3 |

Extended Example 5

The reaction of Example 5 was run successfully for over 1,000. After about 500 hours the flow rate was reduced to about 8.7 gram/hour; after about 1050 hours the flow rate was reduced to about 4.7 gram/hour. DPA conversion and product remained consistently high; the ratio of non-alkylated:mono-alkylated:di-alkylated:tri-alkylated DPA of the fraction collected at 724 hours was 0.4:19.7:75.3:4.3, and the ratio at 1398 hours was 0.5:20.1:74.9:4.4.

Removal of Nonenes from Alkylated DPA—Fractions taken from Examples 4, 6 and 7 were stripped under vacuum and heat by using a rotavap or distillation pot. Unreacted nonenes were readily separated from alkylated DPA. The weights recorded for the samples before and after nonene removal verify the assumption that the GC data relative to the area percentage of nonenes and alkylated DPA recorded in the tables are consistent with the actual mass ratios of nonenes and alkylated DPA. Results are shown in Table 3.

TABLE 3

Product Fractions and Isolations

| | Example 4 | Example 6 | Example 7 |
|---|---|---|---|
| Crude Product Amount (g) | 1095 | 862.0 | 434.8 |
| Product Amount (g) | 775.1 | 629.3 | 306.6 |
| Recovered Nonenes (g) | 308.4 | 217.2 | 126.7 |
| *Crude Product Compositions* | | | |
| Nonenes | 26.01 | 27.43 | 30.37 |
| Nonenes dimer | 0.21 | 0.15 | 0.30 |
| Diphenylamine(DPA) | 0.30 | 0.11 | 0.27 |
| Mono-nonylated DPAs | 12.20 | 14.70 | 13.62 |
| Di-nonylated DPAs | 56.39 | 54.75 | 52.31 |
| Tri-nonylated DPAs | 5.10 | 2.87 | 3.13 |
| *Compositions After Nonene Removal* | | | |
| Nonenes | 0.23 | 0.34 | 0.11 |
| Nonenes dimer | 0.24 | 0.14 | 0.22 |
| Diphenylamine(DPA) | 0.30 | 0.15 | 0.23 |
| Mono-nonylated DPAs | 17.76 | 20.50 | 19.70 |
| Di-nonylated DPAs | 75.05 | 74.77 | 75.26 |
| Tri-nonylated DPAs | 6.42 | 4.11 | 4.49 |

Example 8

Diphenylamine Substituted by Alpha-Methyl Styrene

A stainless-steel tube (1 inch diameter, 13 inches in length) was charged with 106 grams of F-24X BASF catalyst (20-60 mesh), which catalyst was pretreated to remove water. A six point thermocouple recorded the internal temperature of the reaction tube along its length. The reaction temperature was set at 130° C. A 25 psig check valve was attached to the outlet of the tubular reactor and the reaction was run under pressure as in Example 5.

Diphenylamine, alpha-methylstyrene and toluene were mixed in a 1:1.45:1.25 mass ratio and heated in feed flask to about 50° C. The feed line connecting the reaction mixture to the reactor was heated to pre-heat the reactants to about 110° C. The heated reactant mixture was pumped into the reactor at a mass flow rate between 40 to 42 grams per hour. Samples were taken at intervals and analyzed by Gas Chromatography to determine the product and raw material ratio as above. The reactants were pumped through the reactor for a total of 7 hours. Crude product, 292 gram in total was collected. A 253 gram portion of the crude was stripped under vacuum and heat leaving 146.7 grams of isolated product. The distillate toluene had a mass of 90.13 grams. DPA and styrene conversions were both 99-100% and the product is in liquid form and had an amber color. The stripped product's composition is shown below.

| Component | GC area % |
|---|---|
| Diphenylamine | 0.53 |
| α-methyl styrene dimer-1 | 7.85 |
| α-methyl styrene dimer-2 | 0.33 |
| α-methyl styrene dimer-3 | 0.72 |
| Mono-alkylated DPA | 9.15 |
| Di-alkylated DPA | 71.76 |
| Tri-alkylated DPA-1 | 0.21 |
| Tri-alkylated DPA-2 | 4.76 |
| Tri-alkylated DPA-3 | 0.30 |
| Others | 4.40 |

Example 9

N-Phenyl-Alpha-Naphthylamine (PANA) Alkylated by Tetrapropylenes

A stainless-steel tube (1 inch diameter, 13 inches in length) was charged with 106 grams of F-24X BASF catalyst (20-60 mesh), which catalyst was pretreated to remove water. A six point thermocouple recorded the internal temperature of the reaction tube along its length. The reaction tube was set at 155° C. A 25 psig check valve was attached to the outlet of the tubular reactor and the reaction was run under pressure.

Tetrapropylenes and N-phenyl-alpha-naphthylamine were mixed in a 1.75:1 mass ratio, i.e., 2.2:1 mole ratio (alkene: PANA) and heated, from about 60° C. to about 80° C. to avoid the precipitation of PANA (mp=59° C.). The feed line connecting the reaction mixture to the reactor was heated to pre-heat the reactants to about 130° C.

The heated reactant mixture pumped into the reactor at a mass flow rate between 36 and 43 grams per hour (averagely 38 grams per hour on average). Sample product fractions were collected in reagent bottles at ambient temperature. The reactants were pumped through the reactor for a total of 27 hours. Samples were taken at intervals and analyzed by gc to determine the product and raw material ratio. Crude product, 1041 gram in total, was collected. A 272.98 gram portion of crude product was stripped under vacuum and heat leaving 170.23 grams of an isolated amber liquid product, the composition of which is shown below.

| Component | GC area % |
|---|---|
| Tetrapropylene Dimers | 0.84 |
| PANA | 6.80 |
| Mono-$C_{12}$ APAN | 81.14 |
| Di-$C_{12}$ APAN-1 | 6.28 |
| Di-$C_{12}$ APAN-2 | 4.29 |
| Others | 0.6 |

What is claimed:

1. A process for alkylating an aromatic amine comprising:
   a) loading a tubular fixed bed reactor with an acidic bentonite clay,
   b) heating or cooling the reactor at a temperature in a range of from about 140° C. to about 180° C.,
   c) pumping through the acidic bentonite clay in the fixed bed reactor a liquid mixture of diphenylamine and a mixture of propylene oligomers comprising tri-propylene and/or tetra-propylene to yield a mixture of alkylated aromatic amines comprising
   less than 1% by weight, based on all aromatic amines present, of diphenylamine,
   about 15% to about 30%, of mono-alkyldiphenyl amine;
   60% to about 80%, di-alkyldiphenyl amine; and
   0.5 to about 10% of tri-alkyldiphenyl amine.

2. The process according to claim 1 wherein the mixture of propylene oligomers comprises tri-propylene and the product mixture of alkylated aromatic amines is liquid at room temperature.

3. The process according to claim 1 wherein the mixture of propylene oligomers and the diphenylamine are mixed together before being introduced to the fixed bed reactor through the same feed.

4. The process according to claim 1 wherein the mixture of propylene oligomers and the diphenylamine are introduced to the fixed bed reactor separately through different feeds.

5. The process according to claim 3 wherein the mixture of propylene oligomers and the diphenylamine are mixed together in a vessel and heated at temperatures of from about 40° C. up to the first selected reaction temperature before being introduced to the fixed bed reactor.

6. The process according to claim 1 wherein the mole ratio of propylene oligomers to diphenylamine of from about 2:1 to about 4:1.

7. The process according to claim 1, wherein the mixture comprising diphenylamine and a mixture of propylene oligomers is pumped through the acidic bentonite clay in the fixed bed reactor, the product mixture is collected at elevated temperature while excess propylene oligomers are continuously stripped out.

8. The process according to claim 7 wherein the excess propylene oligomers are continuously stripped out and fed back into the reactor.

9. The process according to claim 7 wherein the fixed bed reactor is a tube of a shell and tube heat exchanger filled with the acidic bentonite clay where the shell is used to maintain temperature control of the reaction mixture.

10. The process according to claim 9, wherein the reaction product is fed through heat exchanges as heat exchanger fluid.

* * * * *